US010631880B1

(12) United States Patent
Callahan et al.

(10) Patent No.: US 10,631,880 B1
(45) Date of Patent: Apr. 28, 2020

(54) CANNULATED MODULAR MAGNETIC GLENOID REAMER

(71) Applicant: Innovative Medical Solutions LLC, Shelley, ID (US)

(72) Inventors: Kevin Callahan, Shelley, ID (US); Brandon Peebles, Shelley, ID (US)

(73) Assignee: Innovative Medical Solutions LLC, Shelley, OH (US)

( * ) Notice: Subject to any disclaimer, the term of this patent is extended or adjusted under 35 U.S.C. 154(b) by 251 days.

(21) Appl. No.: 15/367,105

(22) Filed: Dec. 1, 2016

Related U.S. Application Data

(60) Provisional application No. 62/261,693, filed on Dec. 1, 2015.

(51) Int. Cl.
*A61B 17/16* (2006.01)
*A61B 17/17* (2006.01)

(52) U.S. Cl.
CPC ...... *A61B 17/1642* (2013.01); *A61B 17/1684* (2013.01); *A61B 17/17* (2013.01)

(58) Field of Classification Search
CPC ............ A61B 17/1732; A61B 17/1735; A61B 17/1739; A61B 17/1697; A61B 17/17; A61B 17/1684; A61B 17/1642
USPC .......................................... 606/79–85, 96–98
See application file for complete search history.

(56) References Cited

U.S. PATENT DOCUMENTS 2,671,369 A * 3/1954 Clark ...................... B25B 23/12 7/901
2,750,828 A * 6/1956 Wendling ................ B25B 13/06 279/128
3,165,950 A * 1/1965 Gooley ................... B25B 23/12 81/125
5,122,134 A * 6/1992 Borzone ............. A61B 17/164 407/30
RE36,797 E * 8/2000 Eggert .................... B25B 23/12 81/125
6,764,490 B1 * 7/2004 Szabo ................ A61B 17/1666 606/81
7,229,078 B2 * 6/2007 Lechot .............. A61B 17/1666 279/79
7,588,572 B2 * 9/2009 White ................ A61B 17/1666 606/80
8,979,851 B2 3/2015 Fallin et al.
9,737,313 B1 * 8/2017 Sohn ................. A61B 17/1615 606/80

(Continued)

FOREIGN PATENT DOCUMENTS

EP 2449985 A1 5/2012

*Primary Examiner* — Jessica Weiss
(74) *Attorney, Agent, or Firm* — Clayton Howarth, P.C.

(57) ABSTRACT

A glenoid reamer having a rim, a hub located central to the rim, a plurality of cutting blades, each of the blades extending from the rim to the hub, and a first transverse slot and a second transverse slot, wherein the first and second transverse slots are positioned to bisect the rim. The glenoid reamer can be configured to slide over a guide pin and toggle with respect to the guide pin, such that the guide pin is received in the first and second transverse slots and the reamer is substantially parallel with the guide pin. The glenoid reamer can also be configured to toggle with respect to the guide pin, such that the reamer is substantially perpendicular with respect to the guide pin.

27 Claims, 5 Drawing Sheets

100
109a
102
118
110
114
109b
109d
116
104
112
104
106
109c

(56) References Cited

U.S. PATENT DOCUMENTS

2003/0225411 A1* 12/2003 Miller .................. A61B 10/025 606/80
2005/0159751 A1* 7/2005 Berthusen .......... A61B 17/1624 606/80
2007/0191854 A1* 8/2007 Grim .................. A61B 17/1666 606/80
2007/0276393 A1* 11/2007 Bonadei ............. A61B 17/1666 606/80
2007/0276394 A1* 11/2007 Johnson ............. A61B 17/1666 606/80
2008/0140078 A1* 6/2008 Nelson ............... A61B 17/1615 606/80
2011/0144649 A1* 6/2011 Victor ................ A61B 17/1617 606/80
2012/0123419 A1* 5/2012 Purdy ................ A61B 17/1615 606/83
2012/0239043 A1* 9/2012 Lappin ............... A61B 17/1631 606/80
2013/0245631 A1* 9/2013 Bettenga ............ A61B 17/1666 606/91
2015/0073417 A1* 3/2015 Norton ............... A61B 17/1617 606/80

* cited by examiner

CANNULATED MODULAR MAGNETIC GLENOID REAMER

CROSS-REFERENCED APPLICATIONS

This application claims the benefit of U.S. Provisional Application No. 62/261,693, filed Dec. 1, 2015, which is hereby incorporated by reference herein in its entirety, including but not limited to those portions that specifically appear hereinafter, the incorporation by reference being made with the following exception: in the event that any portion of the above-referenced application is inconsistent with this application, this application supercedes said above-referenced application.

STATEMENT REGARDING FEDERALLY SPONSORED RESEARCH OR DEVELOPMENT

Not applicable.

BACKGROUND

1. The Field of the Present Disclosure

The present disclosure relates generally the field of orthopedics, and more particularly to the glenoid component of a total shoulder arthroplasty and the preparation of glenoid bone to receive a glenoid implant.

2. Description of Related Art

The glenohumeral joint, or shoulder joint is comprised of, essentially, a humerus and a scapula, with a glenoid, which is a socket, located on a lateral side of the scapula. The humerus is the upper arm bone and the proximal end of the humerus includes a ball which is received in the glenoid to form a "ball and socket" joint.

As an example, when osteoarthritis is present in a shoulder joint a loss of function often occurs between the glenoid and humerus, resulting from degenerative changes to the cartilage and bony structures of the glenoid and/or humerus. Due to these degenerative changes it is often necessary to replace both the glenoid and humerus. The ball, or head, of the humerus cam be replaced with a stem and head modular implant component, and the glenoid can be replaced with a concave component making up the socket, where the head can articulate.

An object of the present disclosure is to provide a device for preparing the glenoid bone for accepting a glenoid component. Another object of the present invention is to provide a device that can prepare the concavity of the glenoid such that the implant component-to-bone interface is as close to symmetrical as feasibly possible, to assure the optimal opportunity for long term survivorship of the shoulder components.

The features and advantages of the present disclosure will be set forth in the description which follows, and in part will be apparent from the description, or may be learned by the practice of the present disclosure without undue experimentation. The features and advantages of the present disclosure may be realized and obtained by means of the devices, formulations and combinations particularly pointed out in the appended claims. An understanding of the present disclosure will provide an appreciation of the unique and beneficial combination of the engineering sciences and the medical sciences which result in heretofore unavailable advantages.

BRIEF DESCRIPTION OF THE DRAWINGS

The features and advantages of the disclosure will become apparent from a consideration of the subsequent detailed description presented in connection with the accompanying drawings in which.

DETAILED DESCRIPTION

Figure 1:
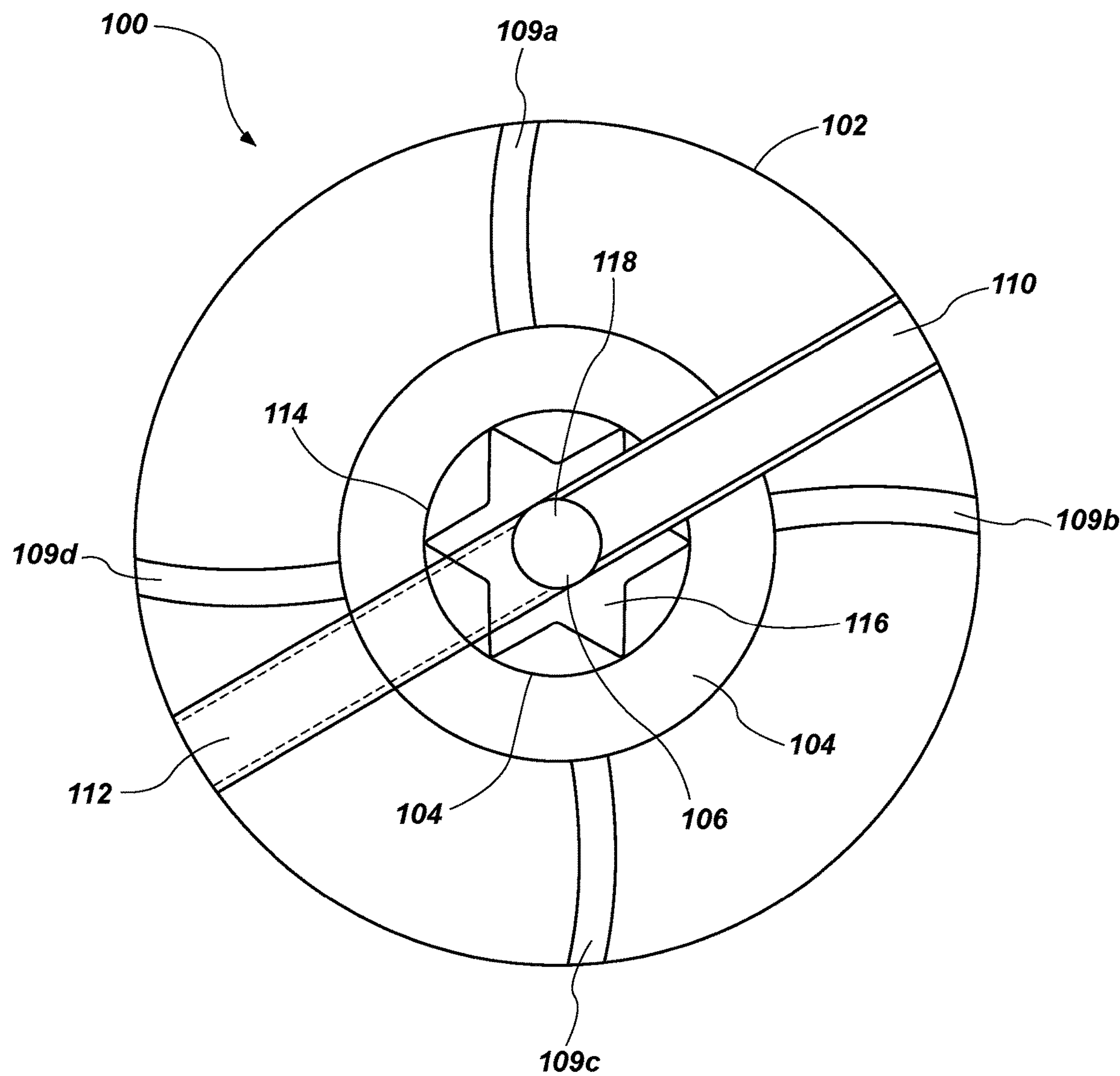
FIG. 1 is a rear view of a glenoid reamer of the present disclosure.

For the purposes of promoting an understanding of the principles in accordance with the disclosure, reference will now be made to the embodiments illustrated in the drawings and specific language will be used to describe the same. It will nevertheless be understood that no limitation of the scope of the disclosure is thereby intended. Any alterations and further modifications of the inventive features illustrated herein, and any additional applications of the principles of the disclosure as illustrated herein, which would normally occur to one skilled in the relevant art and having possession of this disclosure, are to be considered within the scope of the disclosure claimed.

It must be noted that, as used in this specification and the appended claims, the singular forms "a," "an," and "the" include plural referents unless the context clearly dictates otherwise.

In describing and claiming the present disclosure, the following terminology will be used in accordance with the definitions set out below.

As used herein, the terms "comprising," "including," "containing," "characterized by," and grammatical equivalents thereof are inclusive or open-ended terms that do not exclude additional, unrecited elements or method steps.

The present disclosure provides methods and devices providing a cannulated modular glenoid reamer for preparing a glenoid surface to receive an implant, where the glenoid reamer can toggle between a first position to a second position during use, to reduce the impact and potential damage to surrounding tissue during insertion of the glenoid reamer into the shoulder and into the desired position in the glenoid.

Figure 2:
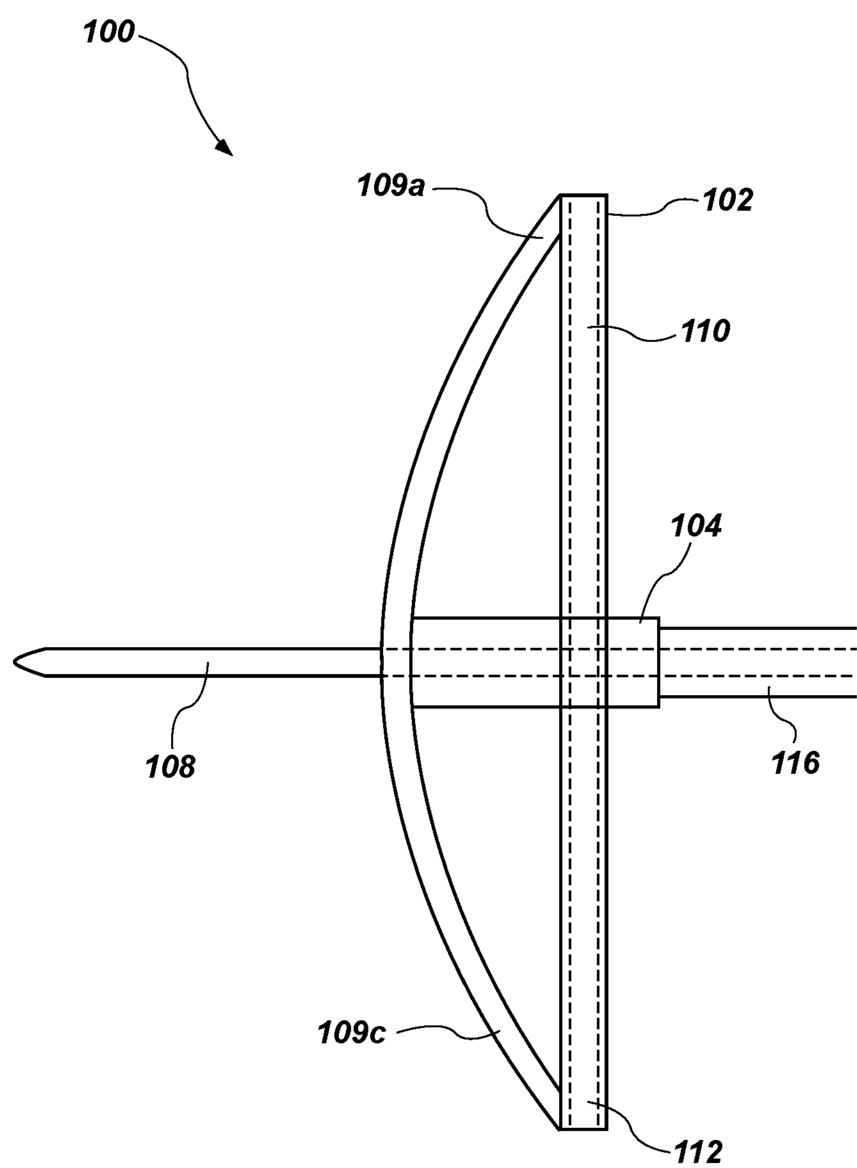
FIG. 2 is a side view of the glenoid reamer of FIG. 1, in a perpendicular position with respect to a guide pin.
Figure 3:
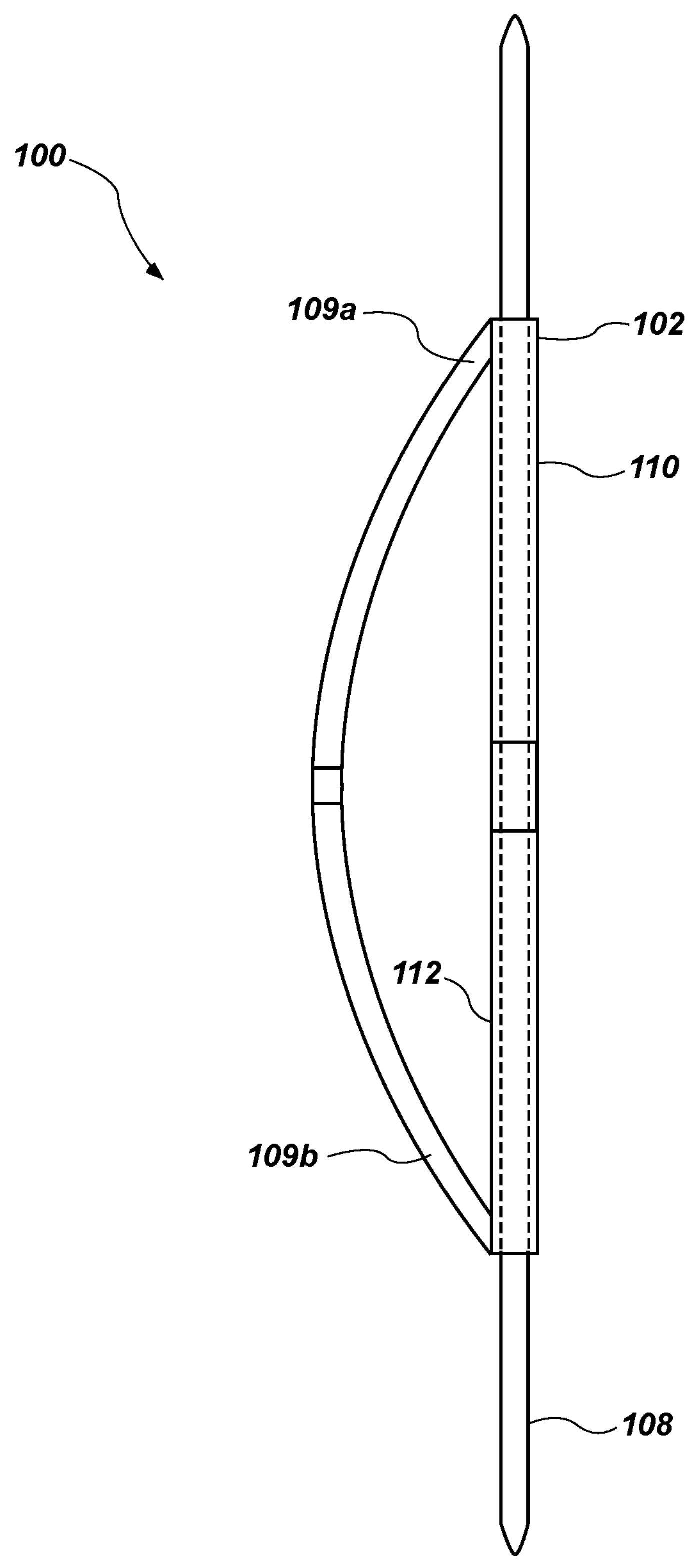
FIG. 3 is a side view of the glenoid reamer of FIG. 1, in a toggled position, substantially parallel with respect to the guide pin.

FIGS. 1-3 illustrate a glenoid reamer, or reamer, 100. The reamer 100 can be used to prepare a glenoid for implantation of an orthopedic implant on a prepared surface of the glenoid during a total shoulder arthroplasty procedure.

The reamer 100 includes a rim 102 that extends continuously and circumferentially in a closed circular shape. The reamer 100 also includes hub 104 is located central to the rim 102. The hub 104 forms a sleeve having a pin hole 106 which is configured to receive an orthopedic pin 108, or guide pin. The pin hole 106 can be of any desired diameter which would enable firm slidable engagement with the guide pin 108, for example 3.2 mm. The guide pin 108 can be inserted and placed centrally in the glenoid, prior to placement and use of the reamer 100, to provide the surgeon or user a guide to assist in positioning the reamer 100 in the correct and desired position with respect to the glenoid.

A series of cutting blades 109*a*, 109*b*, 109*c* and 109*d*, extend between the rim 102 and the hub 104. The cutting blades 109*a*, 109*b*, 109*c* and 109*d*, may be convex in shape, as shown in FIG. 2, to conform to the desired concave surface of the glenoid (not shown). The cutting blades 109*a*, 109*b*, 109*c* and 109*d*, may also include additional cutting blades or fewer cutting blades. The cutting blades 109*a*, 109*b*, 109*c* and 109*d*, are configured to cut away small amounts of bony tissue within the glenoid in order to prepare a smooth, concave surface which can more effectively cooperate with a corresponding implant.

The reamer 100 can also include a first transverse slot 110 and a second transverse slot 112, which together, bisect the rim 102. The first transverse slot 110 is open in a direction away from the cutting blade 109*a*, 109*b*, 109*c* and 109*d*, and the second transverse slot 112 is open in a direction towards the cutting blades 109*a*, 109*b*, 109*c* and 109*d*, opposite to the first transverse slot 110. The first and second transverse slots 110 and 112 are sized to receive the guide pin 108 and enable firm slidable engagement between the transverse slots 110 and 112 and the guide pin 108, for example, the diameter of the transverse slots 110 and 112 may be 3.2 mm or another desired diameter. The transverse slots 110 and 112 enable the reamer 100 to be tilted or toggled to a substantially parallel position with respect to the guide pin 108, as shown in FIG. 3.

The reamer 100 is configured to toggle to a position that is substantially parallel with the guide pin 108 and slide down the length of guide pin 108, after the guide pin 108 has been placed in the desired position in the glenoid. When in the parallel position, the reamer 100 can slide past the proximal humerus (not shown), and toggle back into a perpendicular position, with respect to the guide pin 108, which enables the cutting blades 109*a*, 109*b*, 109*c* and 109*d* to abut the surface needing to be prepared on the glenoid.

The reamer 100 can also include a magnetic insert 114 which can be fixed to, or integrated with, the interior of the hub 104 to improve and secure contact, by magnetic force, between the hub 104 and a reamer shaft 116. The reamer shaft 116 may have a star shaped cross-section, as shown in FIG. 1, a circular cross-section, or other desired shape. The reamer shaft 116 will also be cannulated, having a slot 118, to assure proper alignment and consistent desired positioning of the reamer 100 with respect to the glenoid, during use. The reamer shaft 116 is removable from the hub 104 and can be attached to a mechanical, electrical or manual driver (not shown), to facilitate rotation of the reamer 100 during use.

The ability to toggle the reamer 100 during positioning of the reamer 100 with respect to the glenoid creates a less invasive procedure by not having to perform additional soft tissue releases, in order to gain the exposure needed to prepare the glenoid bone for implant. In contrast, many previously available glenoid reamers can create certain difficulties in relation to soft tissue and existing structures (i.e. the proximal humerus) making it necessary to insert and utilize specific retractors to gain the exposure needed. In these cases the humeral head is often greatly displaced and the surrounding soft tissues often incurs unwanted tension, thus creating more trauma for the patient.

In an exemplary method of using the reamer 100, the reamer 100 can be inserted by hand over the guide pin 108, which has been previously placed by a surgeon. The location and direction of the guide pin 108 is placed axially along the scapula, and centrally on the glenoid face (not shown).

Once the reamer 100 is inserted centrally over the guide pin 108, it is slid down the guide pin 108 until it has come in contact with either soft tissue or the proximal humerus. Once contact is made, the reamer 100 can be toggled to be substantially parallel with the guide pin 108, making it possible to slide the reamer 100 past the soft tissue and proximal humerus without having to do any further releases or causing trauma to the surrounding tissues.

As the reamer 100 is slid past the proximal humerus it can be toggled back to its original orientation (substantially perpendicular to the guide pin 108) and abutted against the glenoid face, thus allowing the glenoid to be prepared without further tissue damage. The reamer shaft 116, which can be connected to a power device will then be inserted over the guide pin 108, and slid into position, locking it into the hub 104 of the reamer 100, which is in place.

The drill (not shown) will then be activated and the reamer 100 and shaft 116 will function as one instrument reaming the concavity of the glenoid, to a depth acceptable to the surgeon, in preparation to receive a component. Once the desired depth is reached, the reamer 100 and shaft 116 can be separated, but still in alignment over the guide pin 108. The shaft 116 can then be removed from the shoulder joint, and the reamer 100 can be removed in the same fashion, with the reamer 100 being toggled as to allow for removal without causing further tissue damage.

Figure 4:
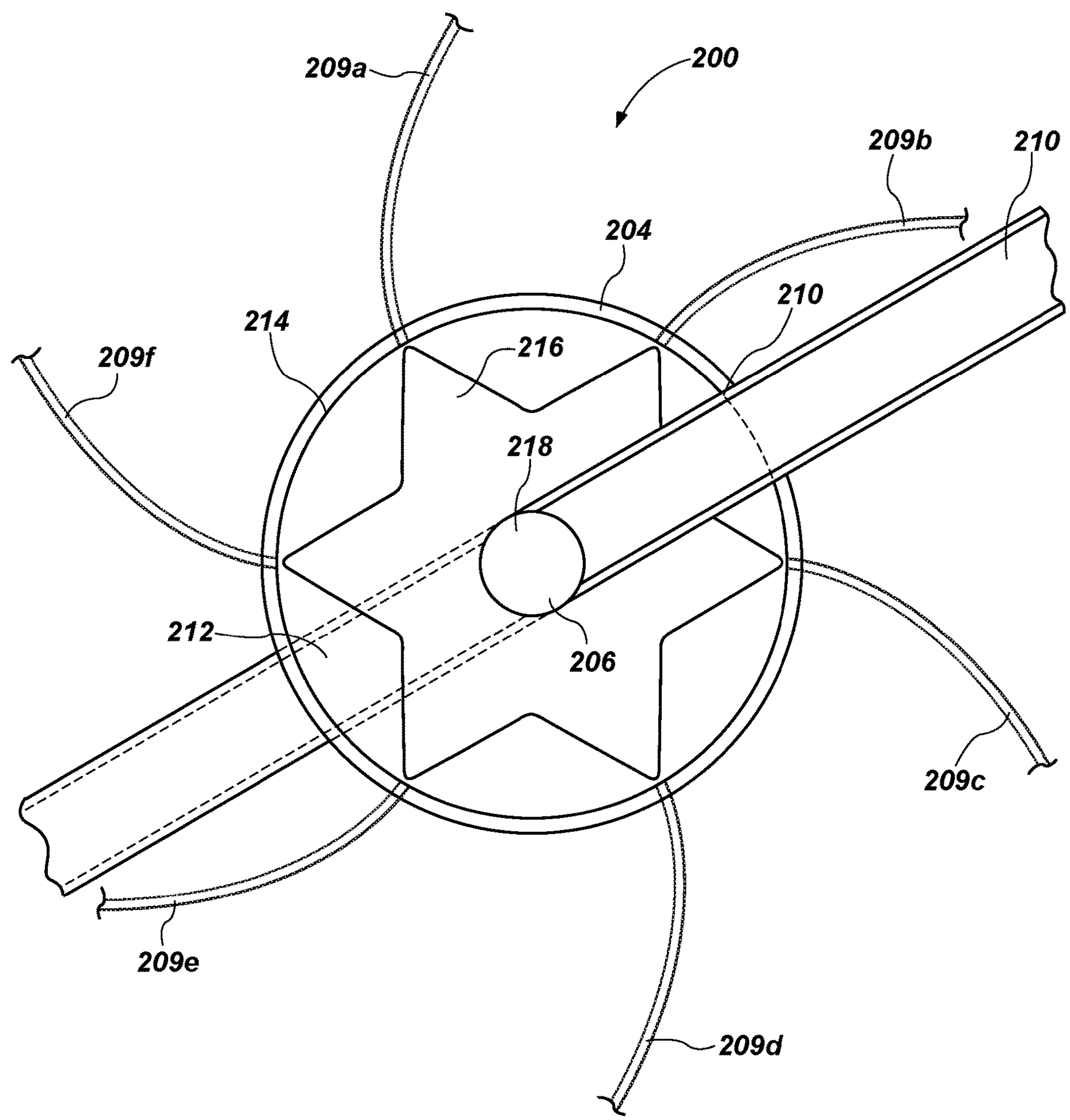
FIG. 4 is a rear view of another glenoid reamer, zoomed in to show the features of the reamer hub.
Figure 5:
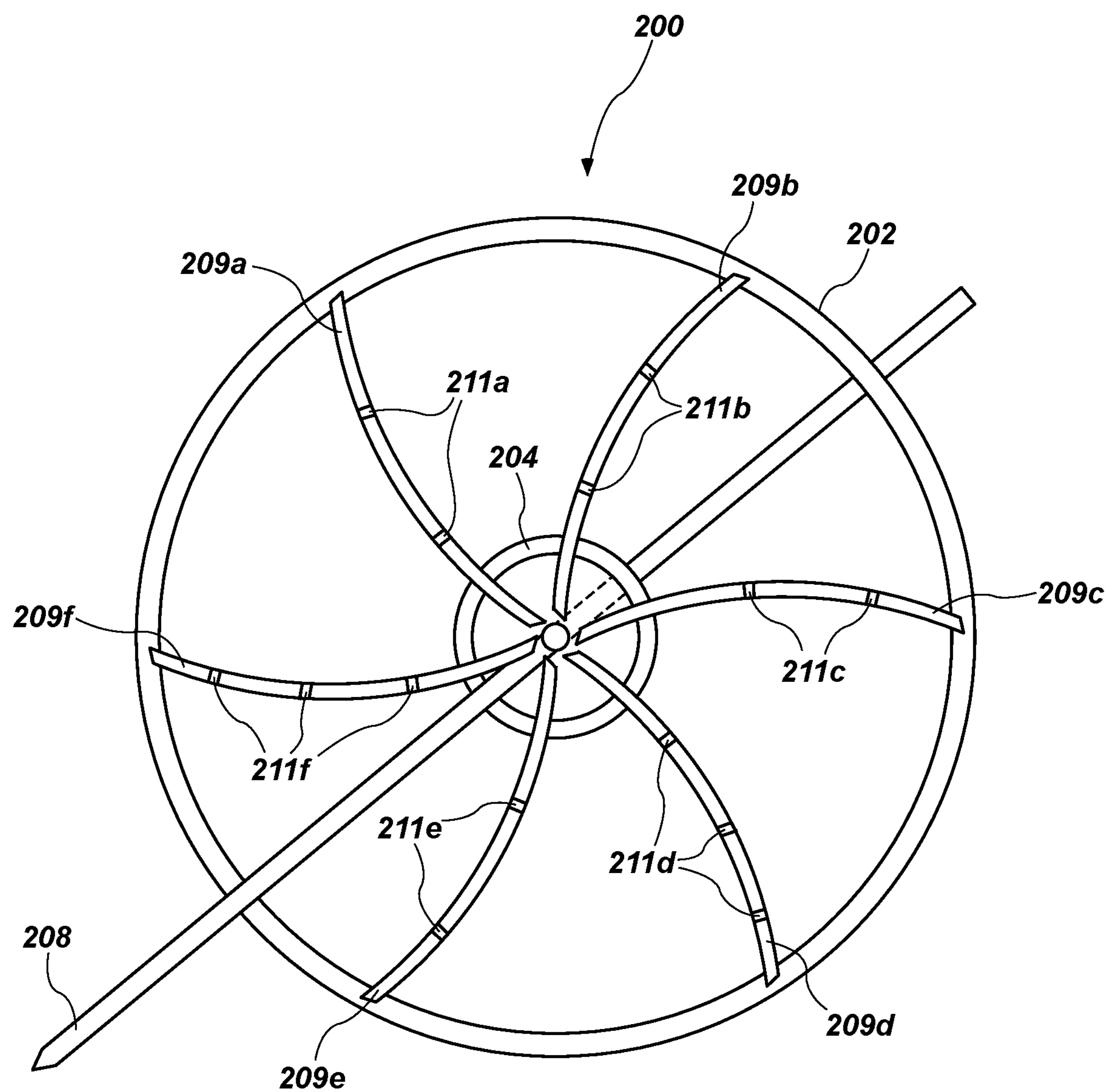
FIG. 5 is a front view of the glenoid reamer of FIG. 4, illustrating a plurality of cutting blades radially extending between a hub and a rim.

FIGS. 4 and 5 illustrate another glenoid reamer, or reamer, 200. The reamer 200 can also be used to prepare a glenoid for implantation of an orthopedic implant on a prepared surface of the glenoid during a total shoulder arthroplasty procedure. The reamer 200 includes a rim 202 that extends continuously and circumferentially in a closed circular shape. The reamer 200 also includes hub 204 which is located central and concentric with the rim 202. The hub 204 forms a sleeve having a pin hole 206, or an alternatively shaped opening, which is configured to receive an orthopedic pin 208, or guide pin. The pin hole 106 can be of any desired diameter which would enable firm slidable engagement with the guide pin 108, for example 3.2 mm or less. The pin hole 208 diameter may also have a diameter of 3 mm-4 mm or 2 mm-5 mm, for example.

The guide pin 208 can be inserted and placed centrally in the glenoid, prior to placement and use of the reamer 200, to provide the surgeon or user a guide to assist in positioning the reamer 200 in the correct and desired position with respect to the glenoid.

A series of cutting blades 209*a*, 209*b*, 209*c*, 209*d*, 210*e* and 209*f* extend between the rim 202 and the hub 204. The cutting blades 209*a*-209*f*, may be convex in shape, as similarly shown in FIG. 2, to conform to the desired concave surface of the glenoid (not shown). The cutting blades 209*a*-209*f*, may also include additional cutting blades or fewer cutting blades. The cutting blades 209*a*-209*f*, are configured to cut away small amounts of bony tissue within the glenoid in order to prepare a smooth, concave surface which can more effectively cooperate with a corresponding implant.

Additionally, each of the cutting blades 209*a*-209*f* include corresponding a plurality of grooves 211*a*-211*f*. Each of the groove 211*a*-211*f* is configured to facilitate improved removal of debris cartilage or bony fragments from the glenoid during the reaming process. The grooves 211*a*-211*f* may be formed or configured to extend substantially perpendicular to a radial direction of each corresponding cutting blade 209*a*-209*f*.

The reamer 200 can also include a first transverse slot 210 and a second transverse slot 212, which together, bisect the rim 202. The first transverse slot 210 is open in a direction away from the cutting blades 209*a*-209*f*, and the second transverse slot 212 is open in a direction towards the cutting blades 209*a*-209*f*, opposite to the first transverse slot 210. The first and second transverse slots 210 and 212 are sized to receive the guide pin 208 and enable firm slidable engagement between the transverse slots 210 and 212 and the guide pin 208, for example, the diameter of the transverse slots 110 and 112 may be 3.2 mm or another desired diameter. Alternatively, the diameters of transverse slots 210 and 212 may be 3 mm-4 mm or 2 mm-5 mm, for example. The transverse slots 210 and 212 enable the reamer 200 to be tilted or toggled to a substantially parallel position with respect to the guide pin 108, as similarly facilitated by the reamer embodiment 100, shown in FIG. 3.

The reamer 200 is configured to toggle to a position that is substantially parallel with the guide pin 208 and slide down the length of guide pin 208, after the guide pin 208 has been placed in the desired position in the glenoid. When in the parallel position, the reamer 200 can slid past the proximal humerus (not shown), and toggle back into a perpendicular position, with respect to the guide pin 208, which enables the cutting blades 209*a*-209*f* to abut the surface needing to be prepared on the glenoid.

The reamer 200 can also include a magnetic insert 214 which can be fixed to, or integrated with, the interior of the hub 204 to improve and secure contact, by magnetic force, between the hub 204 and a reamer shaft 216, or driver.

The reamer shaft 216 may have a star shaped cross-section, as shown in FIG. 4, a circular cross-section, a hexagonal cross-section, or other desired shape. The reamer shaft 216 will also be cannulated, having a slot 218, to assure proper alignment and consistent desired positioning of the reamer 200 with respect to the glenoid, during use. The reamer shaft 216 may be removable from the hub 204 and can be attached to a mechanical, electrical or manual driver (not shown), to facilitate rotation of the reamer 200 during use. Alternatively, the reamer shaft 216 may be configured to be integral or permanently fixed to the hub 204.

The ability to toggle the reamer 200 during positioning of the reamer 200 with respect to the glenoid creates a less invasive procedure by not having to perform additional soft tissue releases, in order to gain the exposure needed to prepare the glenoid bone for implant. In contrast, as noted above, many conventional glenoid reamers can create certain difficulties in relation to soft tissue and existing structures (i.e. the proximal humerus) making it necessary to insert and utilize specific retractors to gain the exposure needed. In these cases the humeral head is often greatly displaced and the surrounding soft tissues often incurs unwanted tension, thus creating more trauma for the patient, which is a problem effectively minimized by the disclosed reamer embodiments.

In an exemplary method of using the reamer 200, the reamer 200 can be inserted by hand over the guide pin 208, which has been previously placed by a surgeon. The location and direction of the guide pin 208 is placed axially along the scapula, and centrally on the glenoid face (not shown).

Once the reamer 200 is inserted centrally over the guide pin 208, it is slid down the guide pin 208 until it has come in contact with either soft tissue or the proximal humerus. Once contact is made, the reamer 200 can be toggled to be substantially parallel with the guide pin 208, making it possible to slide the reamer 200 past the soft tissue and proximal humerus without having to do any further releases or causing trauma to the surrounding tissues.

As the reamer 200 is slid past the proximal humerus it can be toggled back to its original orientation (substantially perpendicular to the guide pin 208) and abutted against the glenoid face, thus allowing the glenoid to be prepared without further tissue damage. The reamer shaft 216, which can be connected to a power device will then be inserted over the guide pin 208, and slid into position, locking it into the hub 204 of the reamer 200, which is in place.

The drill (not shown) will then be activated and the reamer 200 and shaft 216 will function as one instrument reaming the concavity of the glenoid, to a depth acceptable to the surgeon, in preparation to receive a component. Once the desired depth is reached, the reamer 200 and shaft 216 can be separated, but still in alignment over the guide pin 208. The shaft 216 can then be removed from the shoulder joint, and the reamer 200 can be removed in the same fashion, with the reamer 200 being toggled as to allow for removal without causing further tissue damage.

It is to be understood that the above-described arrangements are only illustrative of the application of the principles of the present disclosure. Numerous modifications and alternative arrangements may be devised by those skilled in the art without departing from the spirit and scope of the present disclosure are intended to cover such modifications and arrangements. Thus, while the present disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A glenoid reamer, comprising:

a circumferentially extending rim;

a hub located central to the rim, wherein the hub comprises a sleeve having a longitudinal axis and a hole formed along the longitudinal axis for receiving a guide pin therethrough;

a plurality of cutting blades, each of the plurality of cutting blades extending from the rim to the hub;

a first transverse slot formed through the rim and the hub and a second transverse slot formed through the rim and the hub;

wherein the first and second transverse slots are located opposite each other with respect to the hub such that together the first and second transverse slots bisect the rim, wherein the first and second transverse slots are configured to slidably receive the guide pin, and wherein the glenoid reamer is configured to be inserted over the guide pin and toggle from an original orientation, wherein the guide pin extends through the hole in the hub and where the glenoid reamer is substantially perpendicular to the guide pin, to a second orientation, where the guide pin extends through the first and second transverse slots and where the glenoid reamer is substantially parallel to the guide pin.

2. The glenoid reamer of claim 1, wherein the first transverse slot is open in a direction away from the plurality of cutting blades.

3. The glenoid reamer of claim 2, wherein the second transverse slot is open in a direction towards the plurality of cutting blades.

4. The glenoid reamer of claim 1, wherein each of the plurality of cutting blades are convex in shape.

5. The glenoid reamer of claim 1, wherein the plurality of cutting blades are configured to cut a concave shape in a bone surface.

6. The glenoid reamer of claim 1, wherein the hub includes a magnetic insert.

7. The glenoid reamer of claim 5, wherein the magnetic insert is fixed to an interior of the hub.

8. The glenoid reamer of claim 1, wherein each of the plurality of cutting blades includes at least one groove.

9. The glenoid reamer of claim 8, wherein the at least one groove extends in a direction that is substantially perpendicular to a radial direction of the corresponding cutting blade.

10. A method of using a glenoid reamer, comprising:

providing a guide pin;

providing a glenoid reamer according to claim 1;

sliding the hub of the glenoid reamer over the guide pin; and toggling the glenoid reamer with respect to the guide pin from the original orientation, wherein the guide pin extends through the hole in the hub and where the glenoid reamer is substantially perpendicular to the guide pin, to the second orientation, where the guide pin extends through the first and second transverse slots and where the glenoid reamer is substantially parallel to the guide pin such that the glenoid can be prepared for receiving an implant with minimal trauma to surrounding soft tissue or a proximal humerus.

11. The method of claim 10, wherein the first transverse slot is open in a direction away from the plurality of cutting blades.

12. The method of claim 11, wherein the second transverse slot is open in a direction towards the plurality of cutting blades.

13. The method of claim 10, wherein each of the plurality of cutting blades are convex in shape.

14. The method of claim 10, wherein the plurality of cutting blades are configured to cut a concave shape in a bone surface.

15. The method of claim 10, wherein the hub includes a magnetic insert.

16. The method of claim 15, wherein the magnetic insert is fixed to an interior of the hub.

17. The method of claim 10, wherein each of the plurality of cutting blades includes at least one groove.

18. The method of claim 17, wherein the at least one groove extends in a direction that is substantially perpendicular to a radial direction of the corresponding cutting blade.

19. A surgical system, comprising:

a glenoid reamer, comprising:

a circumferentially extending rim;

a hub located central to the rim, wherein the hub comprises a sleeve having a longitudinal axis and a hole formed along the longitudinal axis;

a plurality of cutting blades, each of the plurality of cutting blades extending from the rim to the hub;

a first transverse slot formed through the rim and the hub and a second transverse slot formed through the rim and the hub, wherein the first and second transverse slots are located opposite each other with respect to the hub such that together the first and second transverse slots bisect the rim;

and a guide pin received by the hub;

wherein, during use, the glenoid reamer is configured to be inserted over the guide pin and toggle from an original orientation, wherein the guide pin extends through the hole in the hub and where the glenoid reamer is substantially perpendicular to the guide pin, to a second orientation, where the guide pin extends through the first and second transverse slots and where the glenoid reamer is substantially parallel to the guide pin.

20. The surgical system of claim 19, wherein the first transverse slot is open in a direction away from the plurality of cutting blades.

21. The surgical system of claim 20, wherein the second transverse slot is open in a direction towards the plurality of cutting blades.

22. The surgical system of claim 19, wherein each of the plurality of cutting blades are convex in shape.

23. The surgical system of claim 19, wherein the plurality of cutting blades are configured to cut a concave shape in a bone surface.

24. The surgical system of claim 19, wherein the hub includes a magnetic insert.

25. The surgical system of claim 24, wherein the magnetic insert is fixed to an interior of the hub.

26. The surgical system of claim 19, wherein each of the plurality of cutting blades includes at least one groove.

27. The surgical system of claim 26, wherein the at least one groove extends in a direction that is substantially perpendicular to a radial direction of the corresponding cutting blade blades.

* * * * *